United States Patent [19]

Masuzawa

[11] Patent Number: 4,928,091

[45] Date of Patent: May 22, 1990

[54] APPARATUS FOR DETECTING POSITION OF MOVING OBJECT

[75] Inventor: Yukikazu Masuzawa, Nishinasuno, Japan

[73] Assignee: Kabushiki Kaisha Toshiba, Kawasaki, Japan

[21] Appl. No.: 217,792

[22] Filed: Jul. 12, 1988

Related U.S. Application Data

[63] Continuation-in-part of Ser. No. 837,070, Mar. 5, 1986, abandoned.

[30] Foreign Application Priority Data

Mar. 6, 1985 [JP] Japan .................................. 60-42841

[51] Int. Cl.$^5$ ............................................. G08B 21/00
[52] U.S. Cl. ..................................... 340/686; 74/435; 74/436; 74/89.2; 74/DIG. 7; 340/540
[58] Field of Search .............................. 340/686, 540; 200/61.14, 61.41, 61.58 R; 74/435, 436, 437, 433, 89.2, 89.21, 89.22, DIG. 7; 116/67 R, 230, 233

[56] References Cited

U.S. PATENT DOCUMENTS

| | | | |
|---|---|---|---|
| 2,920,151 | 1/1960 | Lawick | 200/61.14 |
| 3,562,741 | 2/1971 | McEvoy et al. | 341/15 |
| 3,916,186 | 10/1975 | Raser | 250/231 |
| 3,992,960 | 11/1976 | Rulseh | 74/435 |
| 4,320,480 | 3/1982 | Schonhardt | 200/61.14 |
| 4,445,923 | 5/1984 | Shetterly | 340/686 |
| 4,623,879 | 11/1986 | Woestman | 340/686 |
| 4,699,265 | 10/1987 | Houle | 74/435 |

Primary Examiner—Glen R. Swann, III
Attorney, Agent, or Firm—Finnegan, Henderson, Farabow, Garrett & Dunner

[57] ABSTRACT

In an apparatus for detecting a position of a table, the table moves along a first track having a target position located within a predetermined range. The position detecting apparatus has a movable member and a detecting mechanism. The movable member is movable along a second track. The detecting mechanism detects the movable member when it reaches a predetermined point on the second track. The detecting apparatus further has a transmission mechanism for transmitting the movement of the table to the movable member. The transmission mechanism transmits the movement of the moving object to the movable member at a first transmission ratio moving distance of the movable member/moving distance of the table when the table passes within the predetermined range on the first track, and at a second transmission ratio smaller than the first transmission ratio when the table passes outside the predetermined range on the first track. When the table reaches the target position on the first track, the movable member reaches a predetermined point on the second track, and thus it is detected that the moving object has reached the target position. It can be detected with high precision that the table has reached the target position without increasing the size of the detecting apparatus.

10 Claims, 14 Drawing Sheets

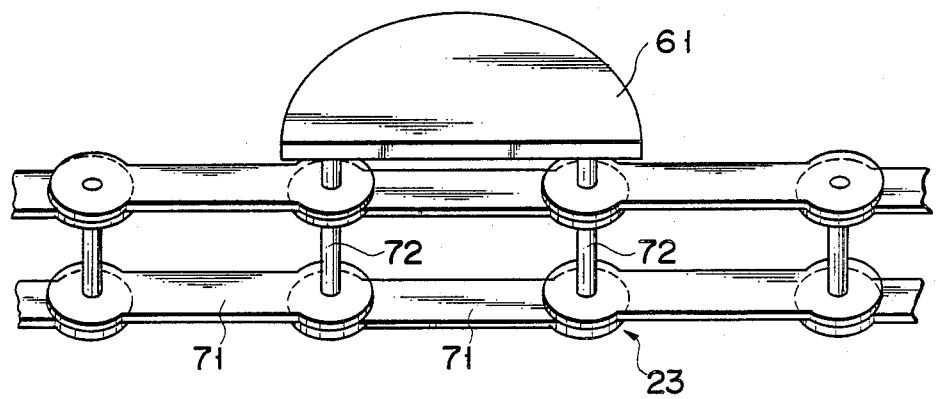
F I G. 9
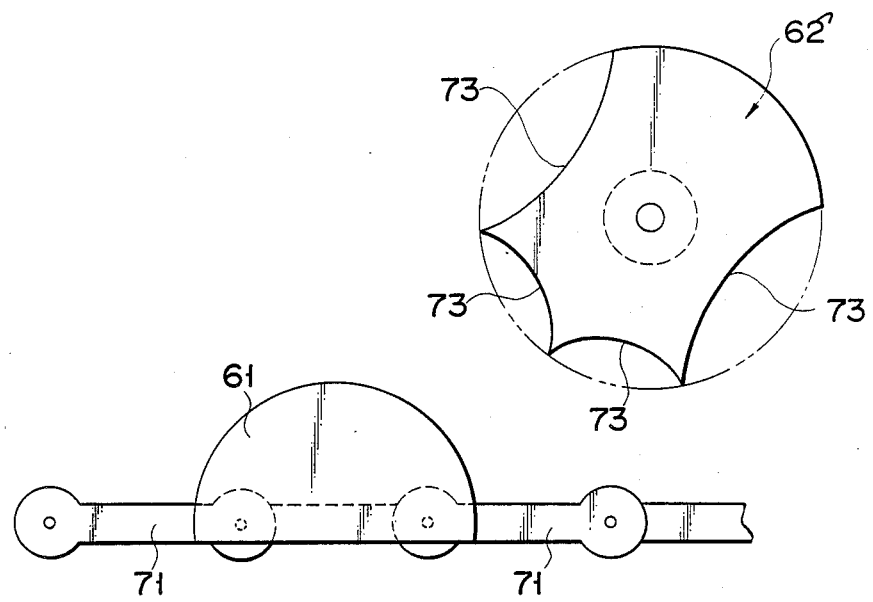
F I G. 10

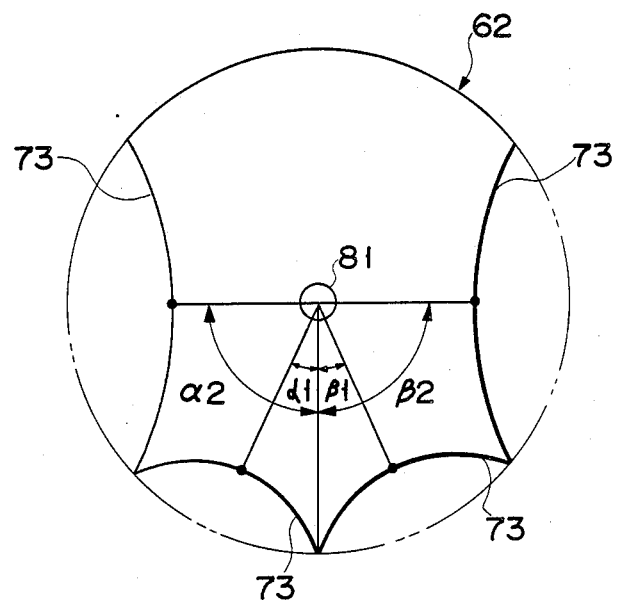
F I G. 13

| POSITION OF TABLE TOP | A2 | A1 | B1 | B2 |
|---|---|---|---|---|
| ROTATION ANGLE OF CAM PLATE | α2 | α1 | β1 | β2 |

FIRST DETECTOR

SECOND

THIRD

FOURTH

FIFTH

SIXTH

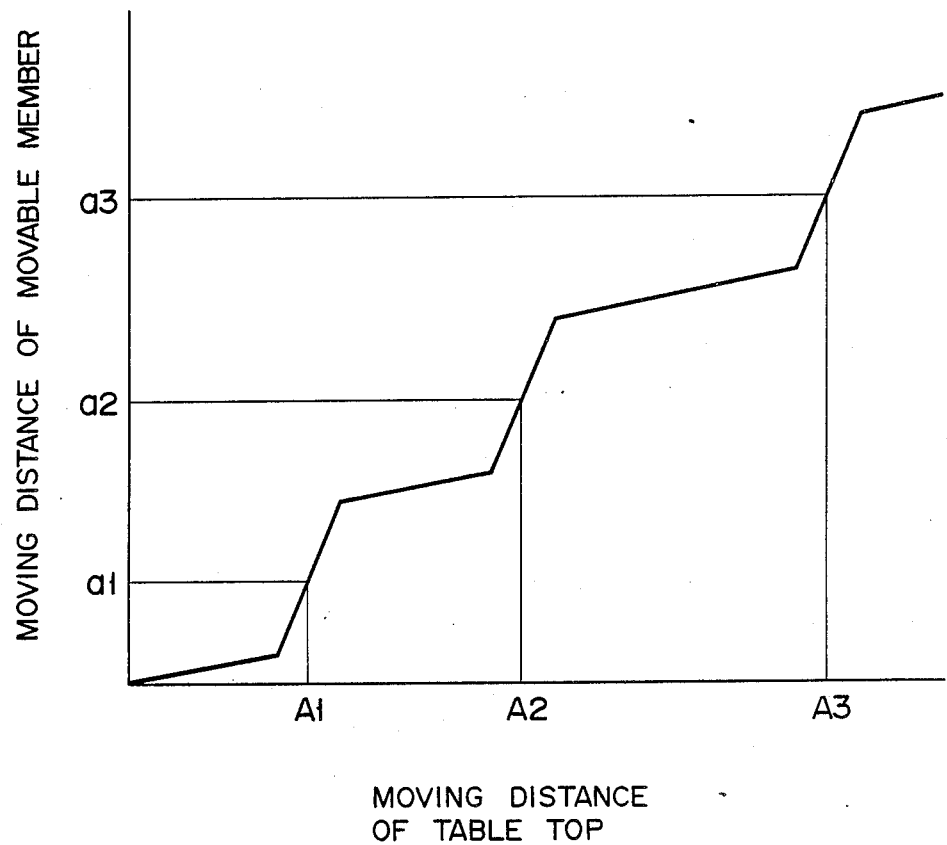
F I G. 18

APPARATUS FOR DETECTING POSITION OF MOVING OBJECT

BACKGROUND OF THE INVENTION

1. Cross Reference to Related Application

This is a continuation-in-part application of patent application Ser. No. 837,070 filed on Mar. 5, 1986, now abandoned.

2. Field of the Invention

The present invention relates to an apparatus for detecting a position of a moving object such as a table top of a raisable bed in an X-ray diagnostic apparatus.

3. Related Art Information

In an X-ray radiographic apparatus, for example, when a patient lies on a raisable bed and an X-ray is emitted from an X-ray tube onto the patient, the X-ray is transmitted through the patient and detected by a spot photographic device or image intensifier (hereinafter referred to as an I.I.) arranged inside the raisable bed. An X-ray image is then formed on a film or displayed on a CRT. However, the X-ray tube can be arranged inside the raisable bed, and the spot photographic device arranged outside it.

FIG. 1 is a schematic side view of raisable bed 2. Bed 2 is installed on floor 4 through base 6. Bed 2 can be raised through about 90 degrees with respect to base 6 and can be laid horizontally. Table top 8 of bed 2 is mounted on main body 10 and can be moved along the direction of arrows 12 with respect to body 10. Spot photographic device 14 is arranged inside bed 2 and can be moved along the direction of arrows 16. An X-ray tube (not shown) is arranged at a position opposite to device 14 so as to interpose table top 8 therebetween. When an X-ray is emitted from the x-ray tube onto a patient lying on table top 8, the X-ray is then transmitted through the patient and is detected by device 14.

In this case, since device 14 is moved inside body 10 of bed 2 along direction 16, various X-ray photographic regions can thus be selected for one diagnostic portion. Table top 8 reciprocates on body 10 along direction 12 and a direction perpendicular thereto, to align the diagnostic portion of the patient with the position of device 14.

In angiography, diagnostic portions include the head, the heart, the coronary arteries, the abdomen, the lower limbs, and the like. Table top 8 must extend as far as positions A2 and A1 in order to obtain angiographic images of the lower limbs and the abdomen, respectively. Table top 8 must be moved to positions B1 and B2 to obtain angiographic images of the heart, the coronary arteries, and the head.

Bed 2 can be raised from the horizontal position indicated by the solid lines to the vertical position indicated by the alternate long and short dashed line in FIG. 1. In this case, when table top 8 is located toward the rear of body 10 (e.g., position B2) and bed 2 is inclined towards the floor, the rear end of table top 8 abuts floor 4. For this reason, an interlock mechanism must be arranged to achieve matching between the inclined angle of bed 2 and the sliding range of table top 8.

In order to control the raising of bed 2 and X-ray photography, the current position of table top 8 must be always detected to fall within one of the ranges between positions A2, A1, B1, and B2. For this purpose, a table top position detecting apparatus is arranged in a conventional X-ray diagnostic apparatus to detect the position of table top 8. The table top position detecting apparatus must retain the current table top position even if the power switch of the X-ray diagnostic apparatus is turned off and must supply the current table top position to a control system for the next diagnosis. Table top 8 is moved within a range as wide as 1 to 1.5 m. The stop positions of table top 8 are not arbitrary positions; they are predetermined. These predetermined positions are not equally spaced. The position detecting apparatus for table top 8 must detect with high precision when table top 8 reaches each one of positions A1, A2, B1, and B2, which are separated by wide and unequal spaces. With these unique requirements, table top positions are mechanically detected in a conventional table top position detecting apparatus.

FIG. 2 is a schematic perspective view showing a moving mechanism for table top 8, and FIG. 3 is a schematic plan view of a conventional table top position detecting apparatus. Table top 8 is supported by a guide mechanism (not shown) and can reciprocate along directions 12. A pair of separated sprockets 21, 22 are arranged along the table top movement directions (i.e., directions 12). Endless chain 23 is looped between sprockets 21, 22. Pulley 26 is coaxially fixed to a rotating shaft of motor 24. Belt 28 is looped around pulleys 26 and 30, which are located opposite each other. The rotation of pulley 30 is reduced by reduction gear 32 and transmitted to sprocket 34. Sprocket 36 is coaxially mounted with sprocket 22. Chain 38 is looped between sprockets 34 and 36. The rotation of motor 24 is reduced by gear 32 and transmitted to sprocket 22, so that chain 23 can be driven along directions 12. This causes table top 8 to reciprocate.

As shown in FIG. 3, sprocket 41 of the conventional table top position detecting apparatus is coaxially mounted with table top drive sprocket 21. Endless chain 43 is looped between sprocket 41 and idler 42. Movable member 45 is mounted on chain 43. When table top 8 reciprocates, movable member 45 is moved along the moving track of chain 43. A plurality of cam switches 44 are arranged at positions a2, a1, b1, and b2 along the moving track of chain 43. Positions a2, a1, b1, and b2 are the positions of member 45 when table top 8 is located at stop positions A2, A1, B1, and B2, respectively. When member 45 reaches one of positions a2, a1, b1, and b2, the corresponding switch 44 is operated so that table top 8 is detected as reaching the corresponding one of stop positions A2, A1, B1, and B2.

In the position detecting apparatus shown in FIG. 3, movable member 45 is moved for a distance in proportion to the moving distance of table top 8. In other words, the movement of table top 8 is transmitted to movable member 45 at a predetermined transmission ratio (moving distance of movable member/moving distance of table top). In order to detect whether table top 8 has reached a target position with high precision, a large transmission ratio may be set. For example, in a case shown in FIG. 4, the transmission ratio = 1 and movable member 45 is moved for a distance equal to that of table top 8. In a case shown in FIG. 5, the transmission ratio = 2 and movable member 45 is moved for a distance twice that of table top 8. Comparing these two cases, if the moving distances of table top 8 of both cases are the same, in the case of FIG. 5, movable member 45 is moved for a distance twice that in the case of FIG. 4. Therefore, in the case of FIG. 5, the moving distance of table top 8 is detected with a precision twice that in FIG. 4. The detection precision in FIG. 5 is thus twice that in FIG. 4. In other words, the larger the transmission ratio, the higher the detection precision.

In the position detecting apparatus shown in FIG. 3, the transmission ratio is always the same. In order to set the transmission ratio N times that of the ordinary case, the total moving distance of movable member 45 must be set to be N times that of the ordinary case, i.e., the length of chain 43 must be set to be N times that of the ordinary case, thereby increasing the size of the detecting apparatus. In other words, when a large transmission ratio is set, although the detection precision is improved, the chain length becomes large, thus increasing the size of the detecting apparatus. In contrast to this, when a small transmission ratio is set, although the size of the detecting apparatus is decreased, the detection precision is not improved.

SUMMARY OF THE INVENTION

It is an object of the present invention to provide an apparatus for detecting a position of a moving object wherein the detection precision of the position of the moving object is improved without increasing the size of the detecting apparatus.

According to the present invention, there is provided an apparatus for detecting a position of a moving object, the moving object moving along a first track having a target position located within a predetermined range, the position detecting apparatus comprising:

a movable member movable along a second track;

detecting means for detecting whether the movable member has reached a predetermined point on the second track; and transmitting means for transmitting a movement of the moving object to the movable member, the transmitting means transmitting the movement of the moving object to the movable member at a first transmission ratio of [moving distance of the movable member/moving distance of the moving object] when the moving object passes within a predetermined range on the first track and at a second transmission ratio smaller than the first transmission ratio when the moving object passes outside the predetermined range on the first track, whereby, when the moving object reaches the target position on the first track, the movable member reaches the predetermined point on the second track, thus detecting that the moving object has reached the target position.

Therefore, according to the present invention, when the moving object passes within the predetermined range on the first track, i.e., when the moving object passes near the target position, the movement of the moving object is transmitted to the movable member at a relatively large first transmission ratio. When the moving object passes outside the predetermined range on the first track, i.e., when the moving object passes a portion other than near the target position, the movement of the moving object is transmitted to the movable member at a relatively small second transmission ratio.

As a result, when the position of the moving object is detected, a high detection precision is set, whereas when the position of the moving object is not detected, the moving distance of the movable member is reduced. Therefore, a high detection precision is set without increasing the total moving distance of the movable member. Namely, the detection precision is improved without increasing the size of the detecting apparatus.

BRIEF DESCRIPTION OF THE DRAWINGS

FIG. 9 is a perspective view showing a chain and a movable piece used in a moving mechanism;

FIG. 10 is a plan view of a cam plate and a movable piece;

FIG. 13 is a plan view of a cam plate;

FIG. 18 is a graph showing a relationship between the moving distances of the movable member and the table top in the fourth embodiment of the present invention.

DETAILED DESCRIPTION OF THE PREFERRED EMBODIMENTS

Figure 6:
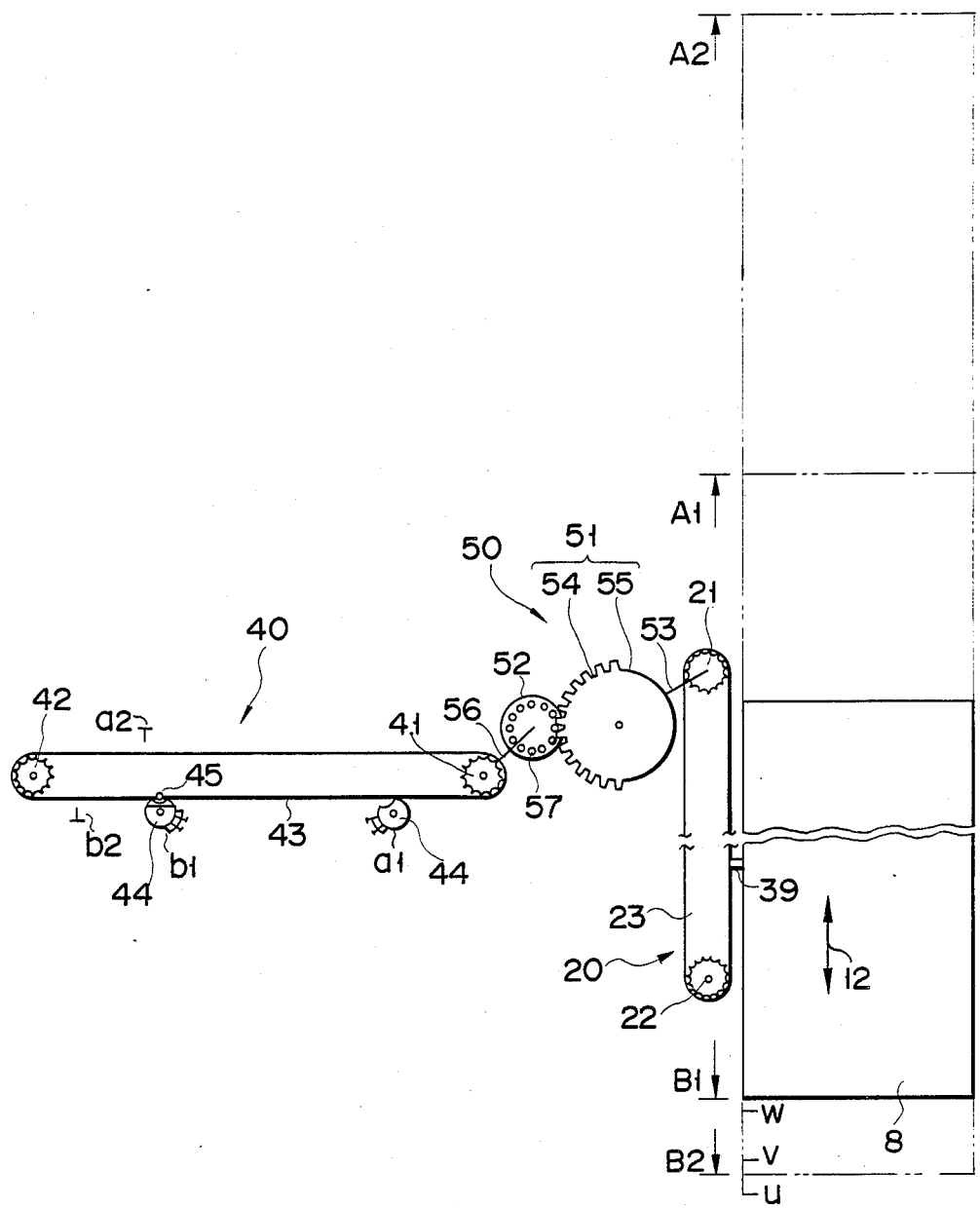
FIG. 6 is a plan view of an apparatus for detecting a position of a table top according to a first embodiment of the present invention.

FIG. 6 shows table top 8 arranged on the raisable bed of an X-ray diagnostic apparatus and moving mechanism 20 for reciprocating table top 8 in the directions indicated by arrows 12. FIG. 6 also shows an apparatus for detecting a position of table top 8 according to a first embodiment of the present invention. The detecting apparatus has detecting mechanism 40 for detecting the position of table top 8 and transmission mechanism 50 for transmitting the movement of table top 8 to detecting mechanism 40.

Figure 1:
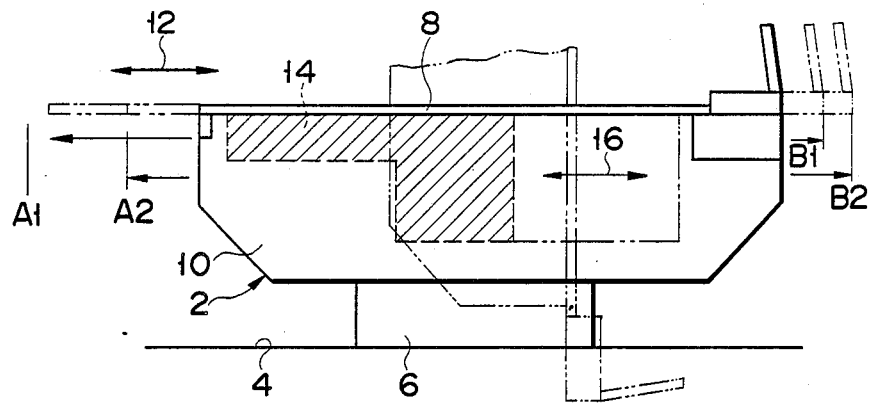
FIG. 1 is a schematic side view of a raisable bed.
Figure 2:
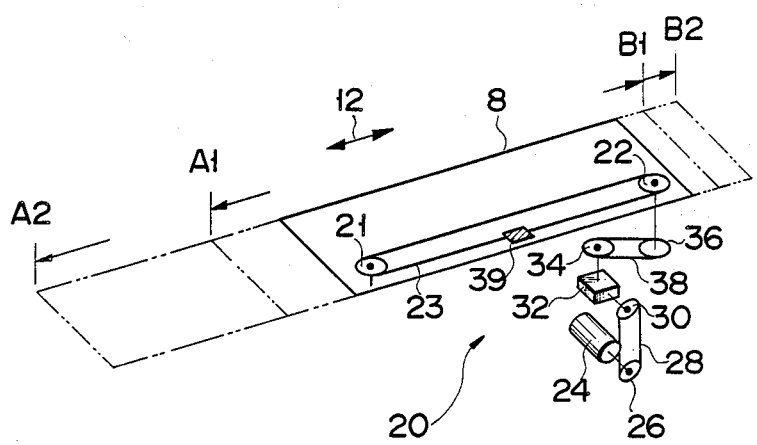
FIG. 2 is a schematic perspective view showing a moving mechanism for a table top.
Figure 3:
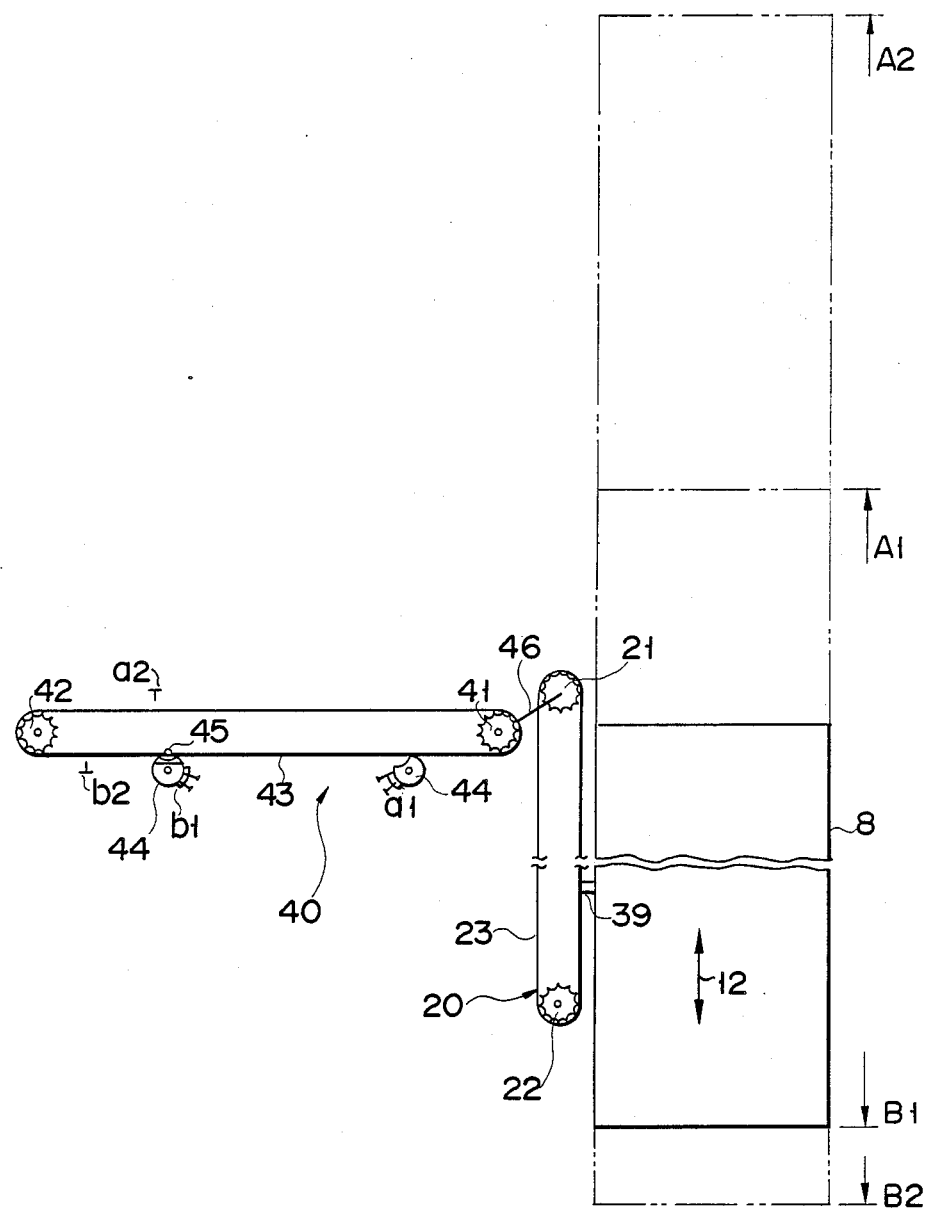
FIG. 3 is a schematic plan view of a conventional table top position detecting apparatus.
Figure 5:
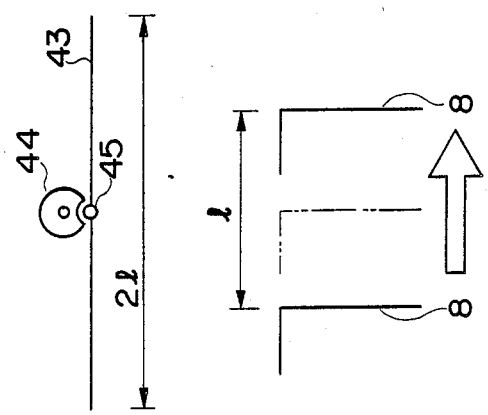
FIGS. 4 and 5 are views comparing the moving distances of a movable member and the table top.
Figure 4:
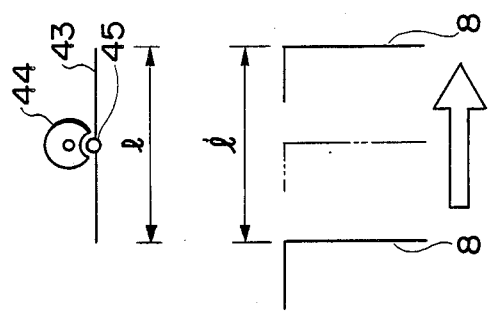

Table top 8, moving mechanism 20, and detecting mechanism 40 of the first embodiment are the same as those of the conventional apparatus shown in FIG. 3. The detecting apparatus of the first embodiment differs from the conventional position detecting apparatus shown in FIG. 3, in that the apparatus of FIG. 3 has transmission mechanism 50. Thus, the conventional position detecting apparatus of FIG. 3 will again be described, and then the position detecting apparatus of the first embodiment will be described.

Moving mechanism 20 and detecting mechanism 40 of the conventional detecting apparatus in FIG. 3 will be described.

Referring to FIG. 3, moving mechanism 20 has a pair of separated sprockets 21 and 22 and endless chain 23 looped between sprockets 21 and 22. Chain 23 and table top 8 are coupled through coupling member 39. Sprocket 22 is rotated by a motor (not shown). Thus, when the motor is driven, chain 23 is moved in the directions of arrows 12, thereby reciprocating table top 8 in these directions. This position detecting apparatus detects whether or not table top 8 has reached an indicated target position (A2, A1, B1, B2).

Detecting mechanism 40 has a pair of sprockets 41 and 42 separated by a predetermined gap and endless chain 43 looped between sprockets 41 and 42. A plurality of cam switches 44 are arranged along chain 43. Movable members 45 for turning on/off switches 44 are mounted on chain 43.

Sprocket 21 of moving mechanism 20 and sprocket 41 of detecting mechanism 40 are coupled through shaft 46. Thus, when chain 23 is rotated to move table top 8, shaft 46 is rotated in accordance with the movement of chain 23 (i.e., the movement of table top 8) to rotate shaft 46, thereby moving chain 43. As a result, movable member 45 moves in response to the movement of table top 8. In other words, the movement of table top 8 is transmitted to movable member 45. The position (a2, a1, b1, and b2) of switches 14 is the same as that of movable member 45 when table top 8 is located at a target position (A2, A1, B1, and B2). Therefore, when table top 8 reaches a target position (A2, A1, B1, and B2), movable member 45 reaches a position (a2, a1, b1, and b2), and a corresponding switch 44 is turned on, thus detecting that table top 8 has reached the target position.

In the conventional detecting apparatus, a decelerator or accelerator is sometimes inserted between moving and detecting mechanisms 20 and 40. However, assume that such a unit is not used in the detecting apparatus of FIG. 3 for the sake of descriptive convenience. In FIG. 3, the numbers of teeth are the same in sprockets 21 and 41, and these sprockets are coupled through shaft 46. Thus, movable member 45 is moved the same distance as that of table top 8. In other words, it is assumed in FIG. 3 that the transmission ratio (moving distance of movable member 45/moving distance of table top 8)=1.

Transmission mechanism 50 used in the position detecting apparatus of the first embodiment will be described with reference to FIG. 6.

Transmission mechanism 50 has two gears 51 and 52. Gear 51 is mounted on input shaft 53 extending from sprocket 21 of moving mechanism 20. Gear 51 has toothed portion 54 on one half portion of the gear surface of gear 51 and toothless portion 55 on the other half portion of the gear surface of gear 51. A plurality of teeth are formed on toothed portion 54, and no teeth are formed on toothless portion 55. Gear 52 is mounted on output shaft 56 extending from sprocket 41 of detecting apparatus 40. A plurality of pins 57 are formed on the periphery of gear 52 at a predetermined pitch. Gear 52 is meshed with toothed portion 54 of gear 51. The number of teeth in toothed portion 54 of gear 51 coincides with the number of pins 57 in gear 52.

Therefore, when gear 51 is rotated by a half turn during the meshing state of toothed portion 54 with gear 52, gear 52 is rotated once. When toothless portion 55 opposes gear 52, even if gear 51 is rotated by a half turn, gear 52 will not be rotated. In other words, transmission mechanism 50 alternately switches between a first transmission ratio (rotation of output shaft 56/rotation of input shaft 53)=2 and a second transmission ratio (rotation of output shaft 56/rotation of input shaft 53)=0 to transmit the rotation of input shaft 53 to output shaft 56.

Therefore, the movement of table top 8 is transmitted to movable member 45 at either one of the first and second transmission ratios that are alternately switched. The relationship between the moving distance of table top 8 and that of movable member 45 (namely, the transmission ratio (moving distance of movable member 45/moving distance of table top 8); to be abbreviated as a transmission ratio hereinafter) is indicated by a solid line in FIG. 7.

Figure 7:
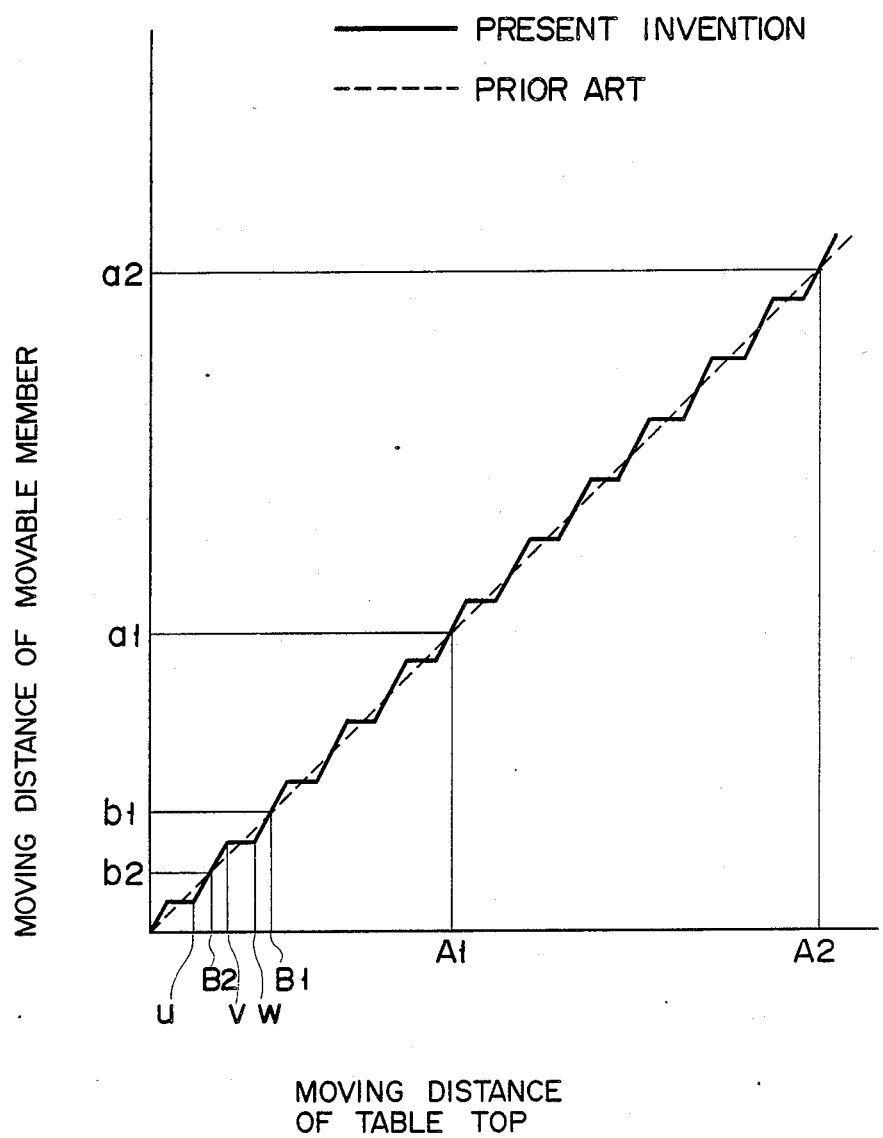
FIG. 7 is a graph showing the relationship between the moving distance of the movable member and that of the table top.
Figure 8:
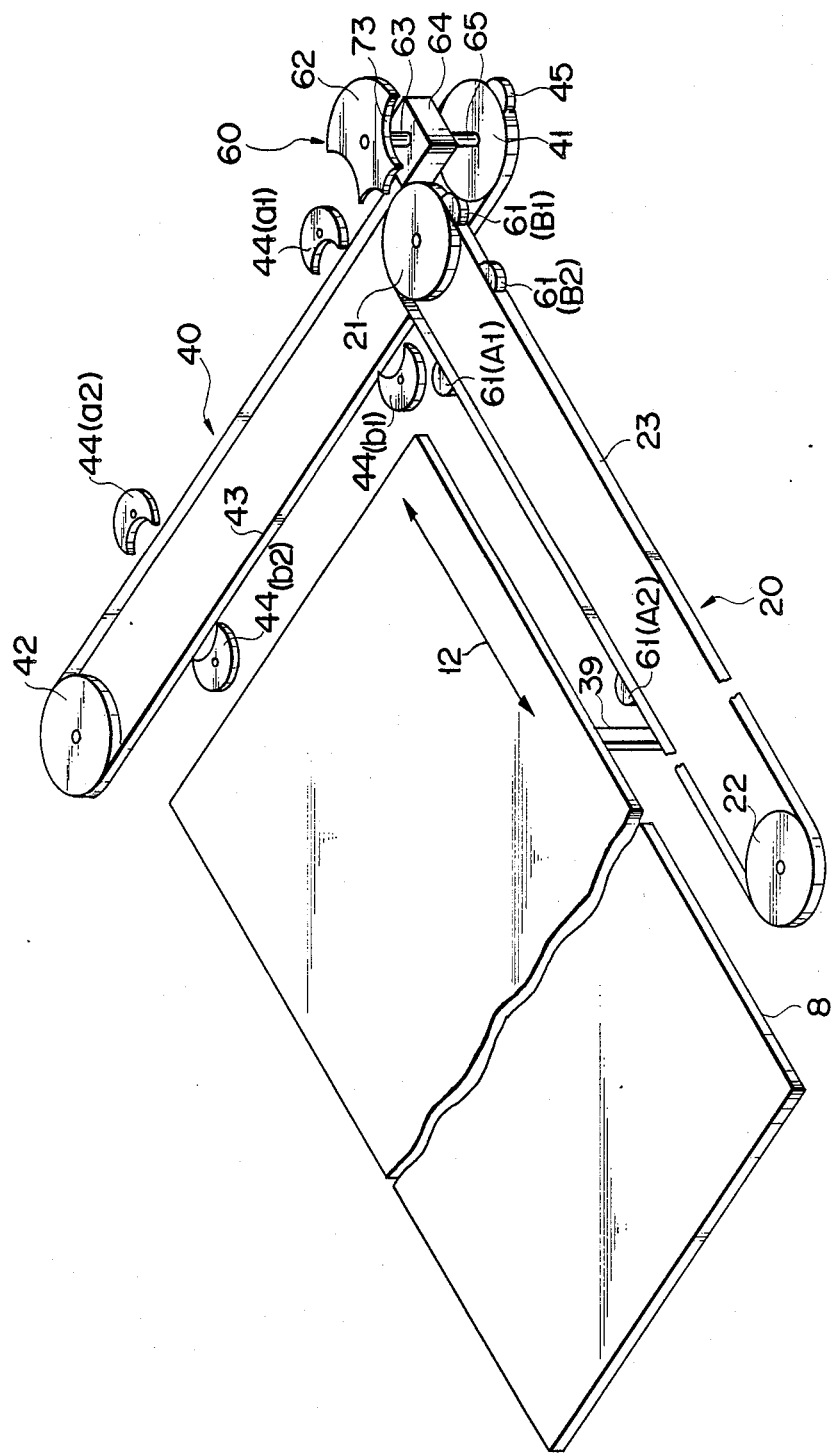
FIG. 8 is a perspective view of an apparatus for detecting a position of a table top according to a second embodiment of the present invention.

Referring to FIG. 7, the case wherein table top 8 moves along position u→B2→v→w→B1 in this order will be described. When table top 8 passes position u→B2→v, its movement is transmitted to movable member 45 at the first transmission ratio (=2). As a result, movable member 45 is moved in response to the movement of table top 8 at the first transmission ratio. When table top 8 reaches target position B2, movable member 45 reaches position b2, and corresponding switch 44 is turned on. When table top 8 passes position v→w, its movement is transmitted to movable member 45 at the second transmission ratio (=0), and thus movable member 45 is not moved. In other words, when table top 8 moves near a target position, the transmission ratio =2; when table top 8 moves in a range not near the target position, the transmission ratio =0.

The present invention aims at determining with high-precision whether or not table top 8 has reached a target position without requiring that the size of the detecting apparatus be increased. Generally, the larger the transmission ratio, the higher the precision of detecting whether or not table top 8 has reached a target position (as described in detail in the background of the invention). In the conventional position detecting apparatus shown in FIG. 3, the transmission ratio is constantly set at 1. This transmission ratio is indicated by a broken line in FIG. 7.

An accelerator is sometimes arranged between the moving and detecting mechanisms in order to increase the transmission ratio. However, in this case, since the transmission ratio itself remains constant, the total moving distance of the movable member must be increased. As a result, the length of the chain of the detecting mechanism is increased, resulting in an increased size of the detecting mechanism. For example, when the transmission ratio of the accelerator =2, the length of the chain of the detecting mechanism must be set to be twice that of the chain of the detecting mechanism in FIG. 3.

Contrastingly, according to the present invention, when table top 8 passes near a position to be detected, the first transmission ratio which is =2 is represented. When table top 8 passes in a range which is not near a position to be detected, the second transmission ratio which is =0 is represented, and movable member 45 is not moved. Therefore, as is apparent from comparing the solid lines and the broken lines in FIG. 7, according to the present invention, although the total moving distance of the movable member is unchanged, the transmission ratio upon the detection is set to be twice as large as that in the case of FIG. 3. Namely, although the detecting mechanism is the same as that in FIG. 3, the transmission ratio is set to be twice as large as that in the case or FIG. 3. Therefore, the detection precision can be improved without requiring that the size of the detecting mechanism be increased. The first transmission ratio of the transmission mechanism can be set at a larger value when the numbers of teeth of these gears are changed. The larger the first transmission ratio, naturally the higher the detection precision.

The second embodiment of the present invention will be described with reference to FIGS. 8 to 11.

Table top 8, moving mechanism 20, and detecting mechanism 40 of the second embodiment are the same as those of the first embodiment. Only transmission mechanism 60 is different from that of the first embodiment. Transmission mechanism 60 has the following arrangement.

A plurality of movable pieces 61 are mounted at various positions of chain 23 of moving mechanism 20. The mounting positions of pieces 61 are such that a single piece 61 is located at the turning point of the chain 23 on the side of sprocket 21 when table top 8 is located at a predetermined target position (A2, A1, B1, or B2). Cam plate 62 supported by shaft 63 is rotatably arranged near sprocket 21. Shaft 63 of cam plate 62 extends parallel to a shaft (not shown) extending from sprocket 21. Shaft 63 is coupled to accelerator 64. Shaft 65 extending from accelerator 64 is coupled to sprocket 41 of detecting mechanism 40.

FIG. 9 is a perspective view of movable piece 61. A plurality of chain chips 71 are coupled by coupling pins 72 to constitute chain 23. Each movable piece 61 has a semicircular shape. A specific pair of pins 72 outwardly extend from chain chips 71. Movable piece 61 is fixed on the extension of chain chips 71.

A plurality of notches 73 are formed in the periphery of cam plate 62. These notches 73 define engaging portions corresponding to movable pieces 61. Therefore, when movable piece 61 fixed on chain 23 reaches the turning point of the chain 23 on the side of sprocket 21, piece 61 is engaged with corresponding notch 73 of cam plate 62 to rotate cam plate 62 for a predetermined amount. The amount of rotation of cam plate 62 is determined depending on the size of notch 73 formed in cam plate 62. An appropriate friction is imparted to cam plate 62 by a belleville spring (not shown) and cam plate 62 is rotated by movable piece 61. However, when piece 61 is not engaged with notch 73 of cam plate 62, cam plate 62 is not inadvertently rotated by the belleville spring.

A plurality of switches 44 of detecting mechanism 40 are arranged at equal intervals.

Figure 11:
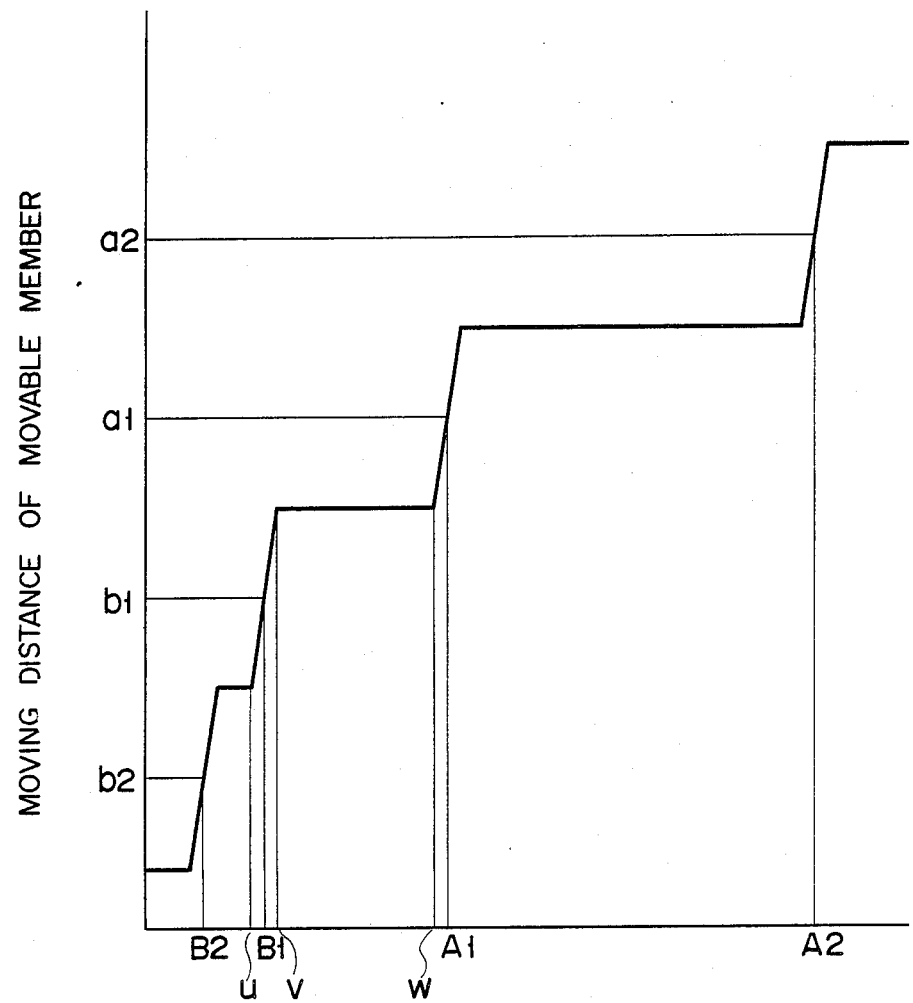
FIG. 11 is a graph showing a relationship between the moving distances of the movable member and the plate top in the second embodiment of the present invention.
Figure 12:
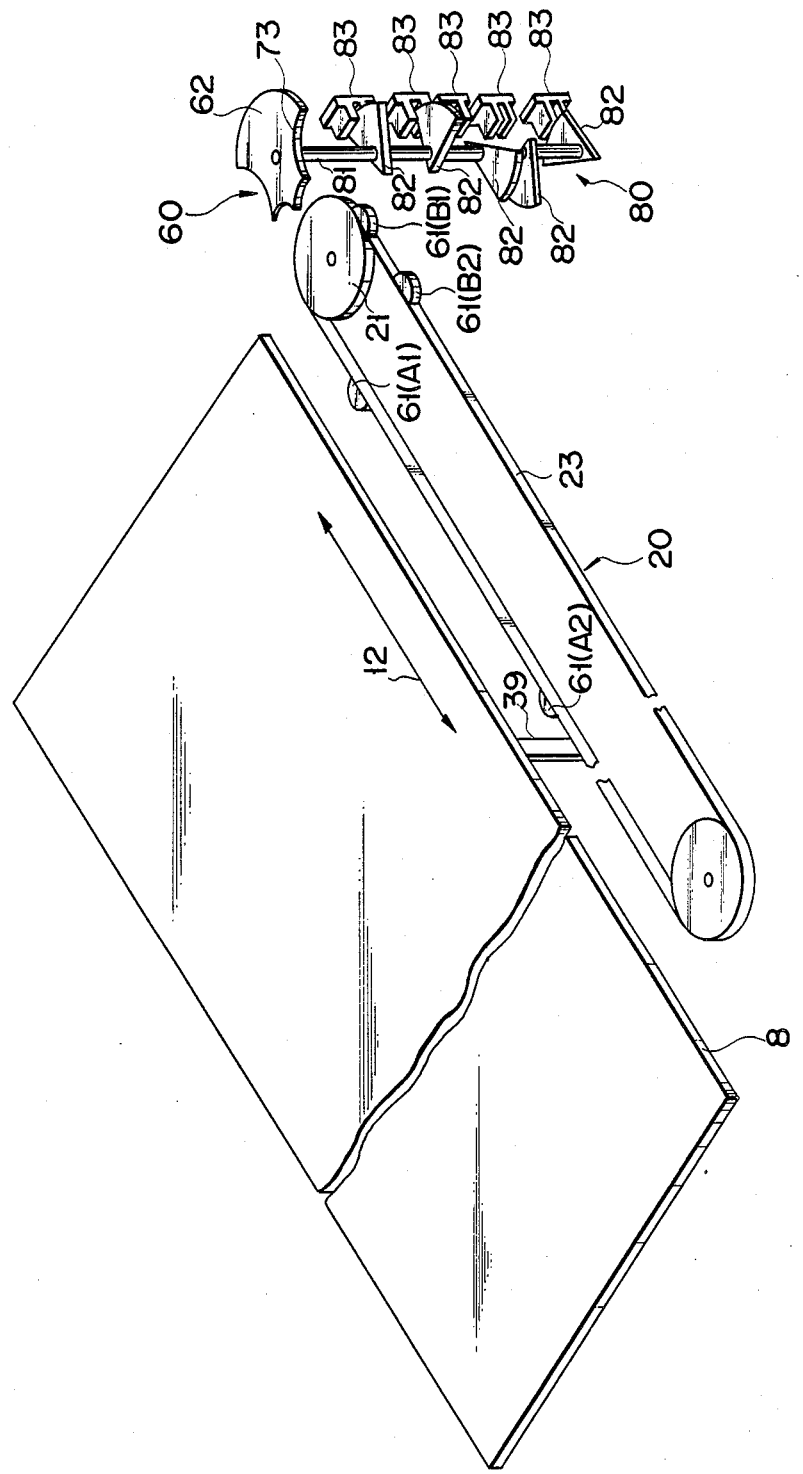
FIG. 12 is a perspective view of an apparatus for detecting a position of a table top according to a third embodiment of the present invention.

The movement of table top 8 is transmitted to detecting mechanism 40 through transmission mechanism 60. FIG. 11 shows a transmission ratio (moving distance of movable member 45/moving distance of table top 8). A case wherein table top 8 moves along position u→B1→v→w will be described.

While table top 8 moves along u→B1→v, movable pieces 61 fixed to chain 23 are engaged with notches 73 of cam plate 62 to rotate cam plate 62. Cam plate 62 is rotated for a period of time after movable pieces 61 start to be engaged with notches 73 and before they complete this engagement. The predetermined amount of rotation of cam plate 62 is transmitted to accelerator ratio 64 through shaft 63 and amplified at a predetermined ratio. As a result, shaft 65 is rotated for a predetermined amount, sprocket 41 of detecting mechanism 40 is rotated, chain 43 is rotated, and as a result movable member 45 is moved for a predetermined distance. When table top 8 reaches target position B1, movable member 45 reaches switch 44 located at position b1 to turn it on. Therefore, while table top 8 passes near a target position, movable member 45 is moved for a distance proportional to the moving distance of table top 8. In other words, while table top 8 passes near a target position, its movement is transmitted to movable member 45 of detecting mechanism 40 at the predetermined first transmission ratio.

While table top 8 moves from position u→w, movable pieces 61 fixed to chain 23 are not engaged with notches 73 of cam plate 62. Therefore, in this case, cam plate 62 is not rotated, and movable member 45 of detecting mechanism 40 is not moved. Namely, while table top 8 passes in a range not near a target position, the transmission ratio is the second transmission ratio =0.

Therefore, also in this second embodiment, the transmission ratio is the predetermined value only when detection is needed, as in the first embodiment, and when detection is not needed, the transmission ratio =0. Therefore, the detection precision is improved without unnecessarily increasing the size of the detecting mechanism.

In the first embodiment, even when table top 8 does not pass near a target position, its movement is sometimes transmitted at the first transmission ratio =2. However, in the second embodiment, only a number of movable pieces 61 necessary for detection need be provided on chain 23. Therefore, the number of movable pieces 61 need only be the number of positions required for detection when the first transmission ratio is set. As a result, if the detection precision is the same, the detecting mechanism of the second embodiment can be smaller than that of the first embodiment.

A third embodiment of the present invention will be described with reference to FIGS. 12 to 15.

In the third embodiment, table top 8, moving mechanism 20, and transmission mechanism 60 are the same as those of the second embodiment. Only detecting mechanism 80 is different from that of the second embodiment.

Detecting mechanism 80 will be described.

Also in the third embodiment, cam plate 62 is not rotated when table top 8 moves in a range not near a target position, in the same manner as in the second embodiment. However, when table top 8 passes near a target position, cam plate 62 is rotated in response to the movement of table top 8. When table top 8 reaches a target position (A2, A1, B1, or B2), cam plate 62 is rotated through a rotating angle ($\alpha 2$, $\alpha 1$, $\beta 1$, or $\beta 2$), as shown in FIG. 13. Therefore, in the third embodiment, a table position detection signal is generated when cam plate 62 has rotated through a rotating angle ($\alpha 2$, $\alpha 1$, $\beta 1$, or $\beta 2$).

The arrangement of detecting mechanism 80 will be described. A plurality of detection pieces 82 are fixed on shaft 81 extending from cam plate 62. The positions of detection pieces 82 are different from each other in the rotating direction of shaft 81. Each of these pieces 82 has a fan-like shape, as shown in FIG. 14, and is fixed on shaft 81 at its wedge side The arcuated side of detection piece 82 is rotated about shaft 81.

A plurality of detectors 83 are provided to oppose corresponding detection pieces 82. Each detector 83 has a pair of detecting portions 84 separated from each other through an appropriate distance. When detection piece 82 is present between detecting portions 84, it is magnetically detected, and a detection signal is input to a signal processor (not shown).

Figures 14, 15:
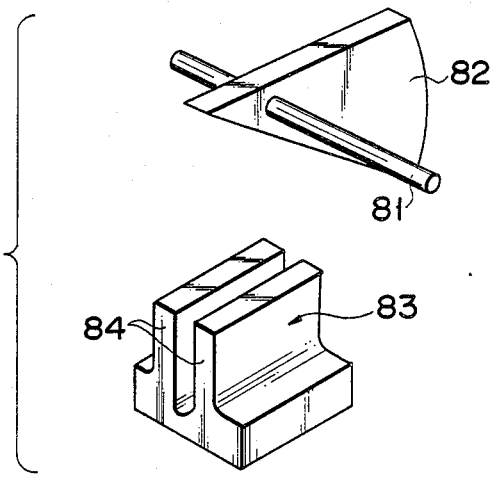
FIG. 14 is a perspective view showing a detecting piece and a detector of a detecting mechanism.
FIG. 15 is a timing chart showing the ON-OFF operation of the detector.

FIG. 15 is a timing chart showing the ON/OFF operations of detectors 83. When each detector 83 is ON, a signal is input to the signal processor; when each detector is OFF, no signal is input to the signal processor. When these detectors 83 are switched, the signal processor determines that cam plate 62 has rotated a rotating angle ($\alpha2$, $\alpha1$, $\beta1$, or $\beta2$), thereby detecting that table top 8 has reached a target position (A2, A1, B1, or B2).

For example, assume that when table top 8 is located between positions A2 and A1 (in the A2-A1 interval) and is moved toward position A1. While table top 8 passes in a range not near position A1, cam plate 62 is not rotated. When table top 8 passes near position A1, movable pieces 61 of chain 23 are engaged with notches 73 of cam plate 62 to rotate cam plate 62. When table top 8 has reached position A1 and cam plate 62 rotates through rotational angle $\alpha1$, the third and sixth detectors are turned off and on, respectively, as shown in the timing chart of FIG. 15. Thus, it is detected that table top 8 reached position A1 and has now entered the A1-B1 interval.

Therefore, also in the third embodiment, since cam plate 62 is rotated only when the position of table top 8 must be detected, the detection precision can be improved without increasing the size of the detecting mechanism. Furthermore, in the third embodiment, the movement of table top 8 is converted into a rotation of cam plate 62 and is detected. Therefore, detectors 83 may be arranged along a single shaft. Thus, the size of detecting mechanism 80 of the third embodiment can be reduced than that of detecting mechanism 40 of the first or second embodiment.

In the third embodiment, when table top 8 is located in, e.g., the A2-A1 interval, the first, second, fourth, and sixth detectors are OFF, and the third and fifth detectors are ON, as shown in the timing chart of FIG. 15. Therefore, it is constantly detected from the ON/OFF combination of these detectors where table top 8 is located, i.e., in the A2-A1, A1-B1, or B1-B2 interval. When examination is ended, table top 8 is stopped in any of these intervals, and the power source of the position detecting apparatus is turned off. When the position detecting apparatus is started for the next examination, cam plate 62 remains at the position where it was at the end of the previous examination. Therefore, when detector 83 is turned on to obtain a detection signal, an interval in which table top 8 is located can be detected from the combination of the detection signals. Namely, in the third embodiment, an interval in which table top 8 is located can be immediately detected upon starting of the position detecting apparatus.

Figure 16:
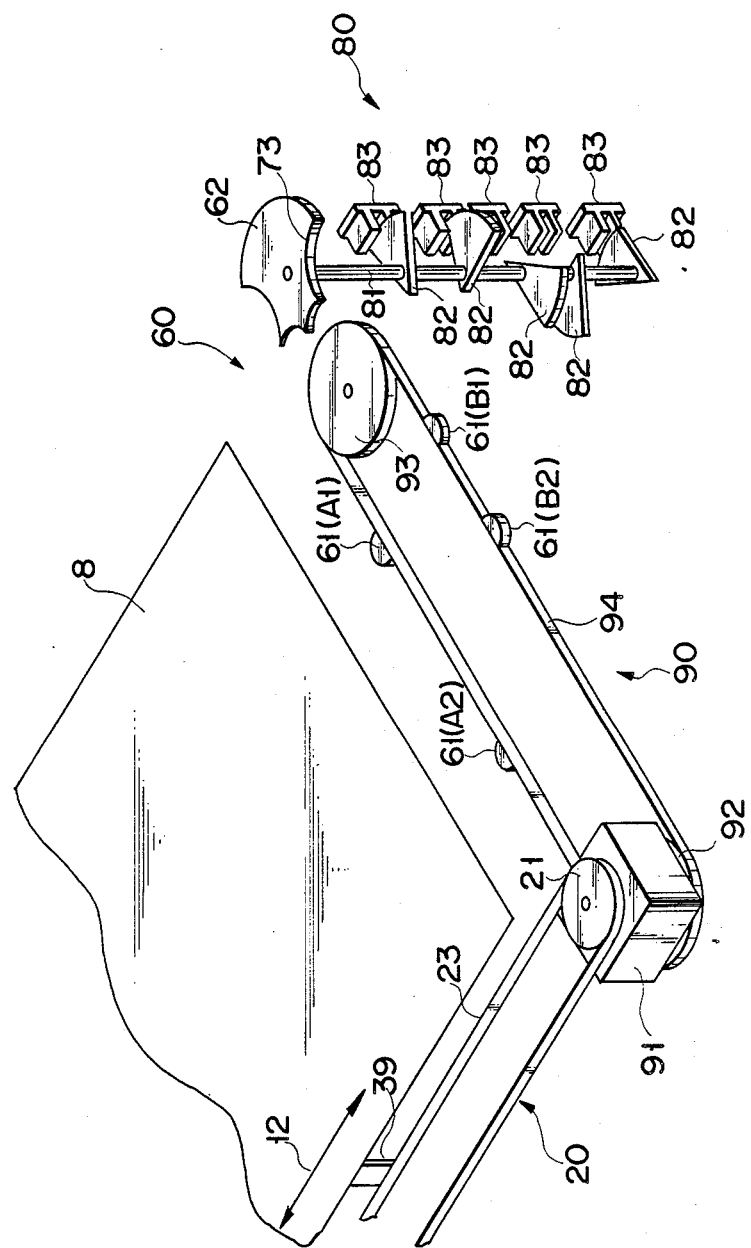
FIG. 16 is a perspective view of an apparatus for detecting a position of a table top according to a modification of the third embodiment of the present invention.

A modification of the third embodiment will be described with reference to FIG. 16.

In this modification, transmission mechanism 60 has sub-transmission mechanism 90 to transmit the movement of table top 8 from moving mechanism 20 to detecting mechanism 80.

Sub-transmission mechanism 90 has decelerator 91 coupled to sprocket 21 of moving mechanism 20, and sprocket 92 coupled to decelerator 91. Another sprocket 93 is provided to oppose cam plate 62 of detecting mechanism 60. Endless chain 93 is looped between these two sprockets 92 and 93. A plurality of movable pieces 61 are arranged at predetermined positions of chain 94.

When chain 23 is rotated, sprocket 21 is rotated, and the movement of table top 8 is transmitted to decelerator 91. The movement of table top 8 is reduced by decelerator 91 at a predetermined deceleration ratio and transmitted to sprocket 92, thereby rotating chain 94. When table top 8 passes near a target position (A2, A1, B1, or B2), movable pieces 61 are engaged with notches 73 of cam plate 62 to rotate cam plate 62 through a predetermined angle. Therefore, even in this modification, since cam plate 62 is rotated only when the position of table top 8 must be detected, the detection precision is improved without increasing size of the detecting mechanism.

Figure 17:
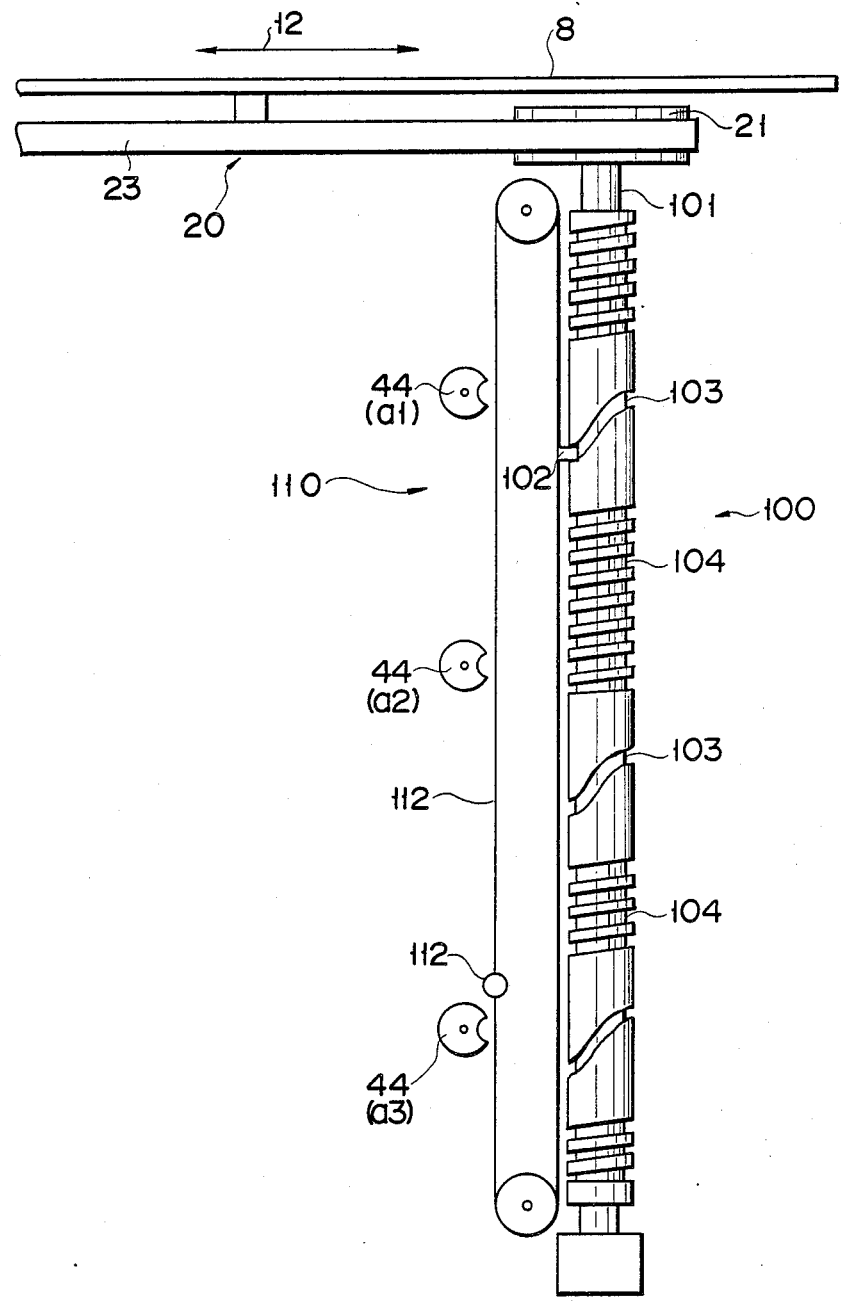
FIG. 17 is a perspective view of an apparatus for detecting a position of a table top according to a fourth embodiment of the present invention.

A fourth embodiment of the present invention will be described with reference to FIGS. 17 and 18.

Table top 8 and moving mechanism 20 or the fourth embodiment are the same as those of any of the first to third embodiments.

Transmission mechanism 100 of the fourth embodiment comprises a feed screw mechanism. More specifically, transmission mechanism 100 has screw shaft 101 on which thread grooves are formed, and cam member 102 to be engaged with the thread grooves. Screw shaft 101 has first thread grooves 103 having a relatively large pitch and second thread grooves 104 having a relatively small pitch. When moving mechanism 20 is driven to move table top 8, screw shaft 101 is rotated. As a result, cam member 102 engaged with the thread grooves is moved in the axial direction. When cam member 102 is engaged with first thread groove 103, cam member 102 is moved for a relatively large distance compared to the actual rotating amount of screw shaft 101. When cam member 102 is engaged with second thread groove 104, cam member 102 is moved for a relatively small distance compared to the actual rotating amount of screw shaft 101. More specifically, in the same manner as in the first to third embodiment, when table top 8 passes near a target position (A3, A2, or A1), its movement is transmitted to cam member 102 at a relatively large first transmission ratio. When table top 8 moves in a range not near a target position (A3, A2, or A1), its movement is transmitted to cam member 102 at a relatively small second transmission ratio.

Detecting mechanism 110 has substantially the same arrangement as that of the first or second embodiment. Cam member 102 is mounted on chain 111 of detecting mechanism 110. Therefore, when the position of table top 8 must be detected, the movement of table top 8 is transmitted to movable member 112 at a first transmission ratio, whereas when the position of table top 8 need not be detected, the movement of table top 8 is transmitted to movable member 112 at a second transmission ratio. FIG. 18 shows the first and second transmission ratios. The detection precision is improved in the fourth embodiment without excessively increasing the size of the detecting mechanism.

In the embodiments described above, the transmission mechanism comprises a mechanism what may be called an "intermittent mechanism" in the field of kinematics of machine. The present invention is not limited to the embodiments described above. A transmission mechanism can be realized by various types of intermittent mechanisms.

What is claimed is:

1. An apparatus for detecting a position of a moving object, said moving object moving along a first track having a target position located within a predetermined range, said position detecting apparatus comprising:
a movable member movable along a second track;
detecting means for detecting whether said movable member has reached a predetermined point on the second track; and
transmitting means for transmitting a movement of said moving object to said movable member, said transmitting means transmitting the movement of said moving object to said movable member at a first transmission ratio of (moving distance of the movable member/moving distance of the moving object) when said moving object passes within a predetermined range on the first track and at a second transmission ratio smaller than the first transmission ratio when said moving object passes outside the predetermined range on the first track,
whereby, when said moving object reaches the target position on the first track, said movable member reaches the predetermined point on the second track, thus detecting that said moving object has reached the target position.

2. An apparatus according to claim 1, wherein the second transmission ratio is 0.

3. An apparatus according to claim 2, wherein said transmitting means includes:
an input shaft for rotating for an amount proportional to the movement of said moving object;
a first gear coupled to said input shaft, said first gear having a toothed portion having a predetermined number of teeth on a portion of a circumference thereof and a toothless portion having no tooth on a remaining portion of the circumference thereof;
a second gear opposing said first gear, capable of being meshed therewith and having a predetermined number of teeth, a proportion of the number of teeth of said toothed portion of said first gear to the number of teeth of said second gear and a proportion of the circumference length of said toothed portion to that of said toothless portion defining the first transmission ratio, said second gear being rotated at the first transmission ratio when meshed with said toothed portion of said first gear and being stopped from rotating when opposing said toothless portion of said first gear; and
an output shaft, coupled to said second gear, for transmitting rotation of said second gear to said movable member,
whereby the movement of said moving object is transmitted to said first gear through said input shaft to rotate said first gear, said toothed portion of said first gear being meshed with said second gear to rotate said second gear at the first transmission ratio when said moving object passes within the predetermined range on the first track, thus transmitting rotation of said second gear to said movable member through said output shaft, and said toothless portion of said first gear opposing said second gear to stop rotation of said second gear when said moving object passes outside the predetermined range on the first track, thus stopping the movement of said movable member.

4. An apparatus according to claim 3, wherein said detecting means includes:
a pair of sprockets, one of which is coupled to said output shaft of said transmitting means;
a chain looped between said pair of sprockets to constitute the second track, said movable member being mounted on said chain; and
a switch arranged along said chain and turned on/off by said movable member, said switch being located at the predetermined point on the second track where said movable member is located when said moving object is located at the target position,
whereby, when said moving object passes within the predetermined range on the first track and said second gear is rotated, rotation of said second gear is transmitted to said chain through said output shaft and said sprockets to move said movable member, and, when said moving object reaches the target position, said movable member reaches the position from which it turns on said switch.

5. An apparatus according to claim 2, further comprising a moving mechanism for moving said moving object, said moving mechanism having a pair of sprockets, a chain looped between said pair of sprockets, and a coupling member for coupling said chain and said moving object; whereby, when one of said sprockets is rotated, said chain is rotated to move said moving object.

6. An apparatus according to claim 5, wherein said transmitting means includes:
a movable piece mounted on said chain of said moving mechanism;
a cam plate, arranged to oppose said one of said sprockets of said moving mechanism and to be rotatable about a rotating axis, said cam plate having a notch formed in a periphery thereof to engage with said movable piece, said movable piece rotating said cam plate only when said chain of said moving mechanism is rotated and said movable piece is engaged with said notch, a moving distance of said movable piece and a rotating angle of said cam plate when said movable piece is engaged with said notch defining the first transmission ratio; and
means for transmitting rotation of said cam plate to said movable member,
whereby, when said moving object passes within the predetermined range on the first track, said movable piece is engaged with said notch of said cam plate to transmit the movement of said moving object to said cam plate at the first transmission ratio, thus transmitting rotation of said cam plate to said movable member, and, when said moving object passes outside the predetermined range on the first track, said movable piece is disengaged from said cam plate to stop said cam plate, thus stopping said movable member.

7. An apparatus according to claim 5, wherein said transmitting means includes:
a movable piece mounted on said chain of said moving mechanism; and
a cam plate, arranged to oppose said one of said sprockets of said moving mechanism and to be rotatable about a rotating axis, said cam plate having a notch formed in a periphery thereof to engage with said movable piece, said movable piece rotating said cam plate only when said chain of said moving mechanism is rotated and said movable piece is engaged with said notch, a moving distance of said movable piece and a rotating angle of said cam plate when said movable piece is engaged with said notch defining the first transmission ratio,
whereby, when said moving object passes within the predetermined range on the first track, said movable piece is engaged with said notch of said cam plate to transmit the movement of said moving object to said cam plate at the first transmission ratio, and, when said moving object passes outside the predetermined range on the first track, said movable piece is disengaged from said cam plate to stop said cam plate, the second track of said movable member is circularly formed around the rotating axis of said cam plate, so that a movement of said movable member corresponds to rotation of said cam plate, and said detecting means includes means for determining whether or not said cam plate is rotated through a predetermined angle, whereby, when said moving object reaches the target position on the first track, it is determined if said cam plate has been rotated through the predetermined angle.

8. An apparatus according to claim 7, wherein said determining means includes:

a shaft extending from said cam plate along the rotating axis;

a detection piece mounted on said shaft; and a detector for detecting whether said detection piece has been rotated through the predetermined angle.

9. An apparatus according to claim 8, wherein said detector has a pair of detecting portions at a predetermined distance from each other, and magnetically detects said detection piece when said detection piece is interposed between said detecting portions.

10. An apparatus according to claim 1, wherein said transmitting means includes:

a screw shaft rotated in response to the of said moving object, said screw shaft having first thread grooves formed at a predetermined pitch and second thread grooves formed at a pitch smaller than the pitch of said first thread grooves, the pitch of said first thread grooves defining the first transmission ratio and the pitch of said second thread grooves defining the second transmission ratio;

a cam member engaged with said first and second thread grooves of said screw shaft and moved along said screw shaft when said screw shaft is rotated; and means for transmitting the movement or said cam member to said movable member, whereby said screw shaft transmits the movement of said moving object to said movable member at the first transmission ratio when said moving object passes within the predetermined range on the first track, and at the second transmission ratio when said moving object passes outside the predetermined range on the first track.

* * * * *